United States Patent
Pujos

(10) Patent No.: US 11,083,683 B2
(45) Date of Patent: Aug. 10, 2021

(54) TOPICAL COMPOSITION

(71) Applicant: Coty Inc., New York, NY (US)

(72) Inventor: Muriel Pujos, West New York, NJ (US)

(73) Assignee: Coty Inc., New York, NY (US)

( * ) Notice: Subject to any disclaimer, the term of this patent is extended or adjusted under 35 U.S.C. 154(b) by 0 days.

(21) Appl. No.: 16/340,861

(22) PCT Filed: Oct. 27, 2017

(86) PCT No.: PCT/US2017/058801
§ 371 (c)(1),
(2) Date: Apr. 10, 2019

(87) PCT Pub. No.: WO2018/081591
PCT Pub. Date: May 3, 2018

(65) Prior Publication Data
US 2019/0231670 A1    Aug. 1, 2019

Related U.S. Application Data

(60) Provisional application No. 62/453,402, filed on Feb. 1, 2017, provisional application No. 62/414,332, filed on Oct. 28, 2016.

(51) Int. Cl.
*A61K 8/67*    (2006.01)
*A61K 8/92*    (2006.01)
*A61K 8/9783*  (2017.01)
*A61Q 19/08*   (2006.01)
*A61Q 19/02*   (2006.01)

(52) U.S. Cl.
CPC .............. *A61K 8/671* (2013.01); *A61K 8/922* (2013.01); *A61K 8/925* (2013.01); *A61K 8/9783* (2017.08); *A61Q 19/08* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 6,471,972 B1 | 10/2002 | Bonte et al. | |
| 7,968,129 B2* | 6/2011 | Golz-Berner | A61K 8/042 424/1.21 |
| 2004/0022818 A1 | 2/2004 | Cho et al. | |
| 2008/0139507 A1* | 6/2008 | Gupta | A61K 8/26 514/63 |
| 2008/0279885 A1* | 11/2008 | Mrue | A61K 8/72 424/195.18 |
| 2009/0175808 A1 | 7/2009 | Galley et al. | |
| 2011/0229538 A1 | 9/2011 | Matravers et al. | |
| 2014/0271509 A1* | 9/2014 | Claiborne | A61K 8/97 424/62 |
| 2017/0100323 A1* | 4/2017 | Matravers | A61K 47/34 |
| 2018/0110721 A1* | 4/2018 | Bell | A61K 8/9789 |
| 2018/0126136 A1* | 5/2018 | Brown | A61M 35/003 |
| 2018/0235232 A1* | 8/2018 | Moeller | A61K 8/19 |
| 2018/0263894 A1* | 9/2018 | Chadwick | A61K 8/37 |
| 2018/0318165 A1* | 11/2018 | Donda | A61F 13/00 |

FOREIGN PATENT DOCUMENTS

| | | |
|---|---|---|
| DE | 102004039631 A1 | 3/2006 |
| WO | WO-9962481 A1 | 12/1999 |
| WO | WO-2015187921 A1 | 12/2015 |
| WO | WO-2018081591 A1 | 5/2018 |

OTHER PUBLICATIONS

Product information obtained from the website https://www.philosophyskincare.co.uk/miracle-worker-retinoid-pads.html (Year: 2011).*
Huang et al ("Biological and Pharmacological Activities of Squalene and Related Compounds: Potential Uses in Cosmetic Dermatology", Molecules, vol. 14 (2009), p. 540-554). (Year: 2009).*
An internet article "10 Reasons to Start Putting Coconut Oil on Your Face & Skin" by Susan Patterson (https://www.naturallivingideas.com/coconut-oil-face/). (Year: 2016).*
"Database accession No. 1420925", XP002777360, (Sep. 1, 2014).
"Database accession No. 2665313", XP002777359.
"Database accession No. 3233459", XP002777358, (Jul. 1, 2015).
"Database accession No. 3626565", XP002777361, (Jan. 1, 2016).
"International Application Serial No. PCT/US2017/058801, International Search Report dated Mar. 5, 2018", 4 pgs.
"International Application Serial No. PCT/US2017/058801, Written Opinion dated Mar. 5, 2018", 9 pgs.
"International Application Serial No. PCT/US2017/058801, International Preliminary Report on Patentability dated May 9, 2019", 11 pgs.

* cited by examiner

*Primary Examiner* — Sin J Lee
(74) *Attorney, Agent, or Firm* — Schwegman Lundberg & Woessner, P.A.

(57) ABSTRACT

A topical composition comprising at least one retinoid, alfalfa extract, and at least one carrier and uses thereof.

8 Claims, 1 Drawing Sheet

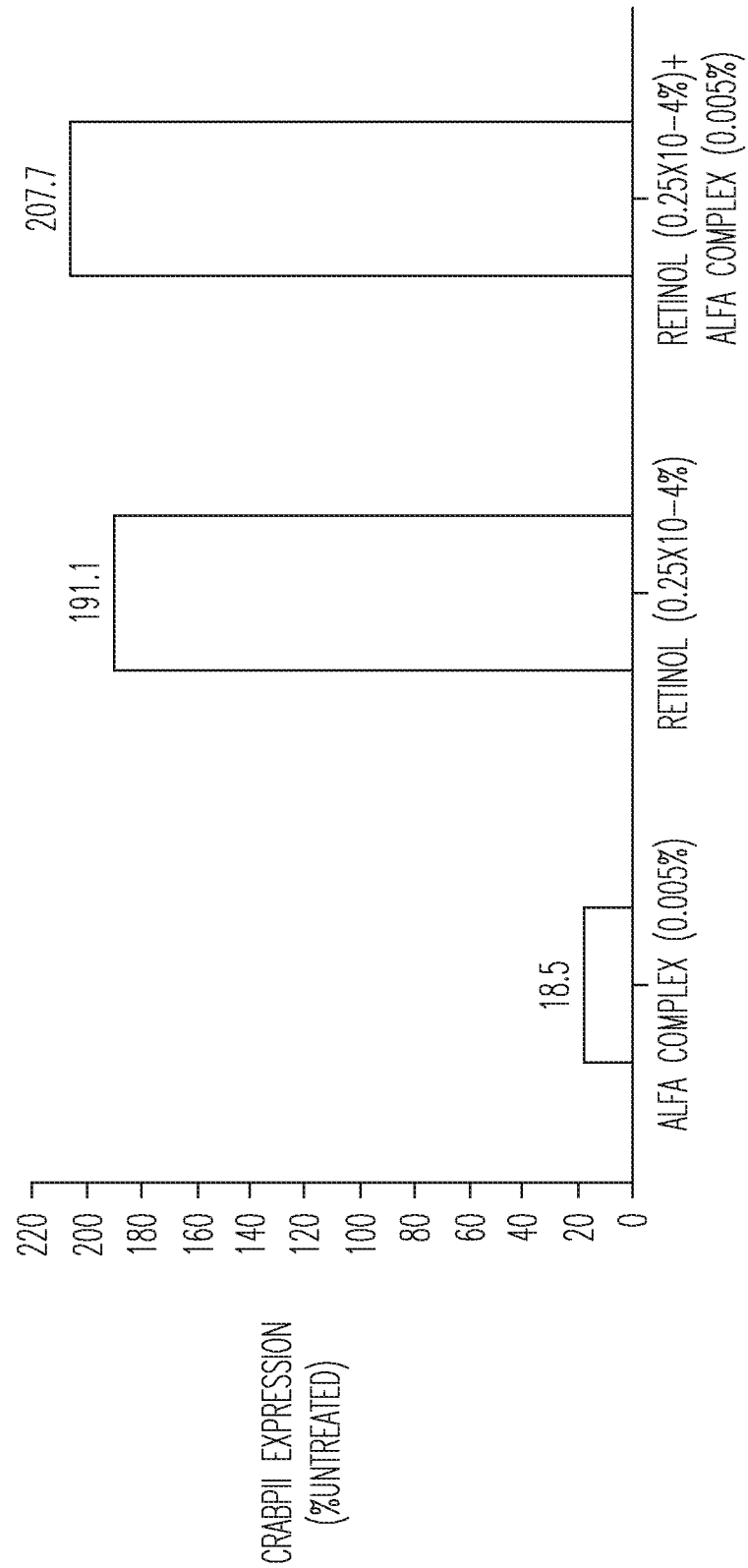

TOPICAL COMPOSITION

PRIORITY

This application is a U.S. National Stage Filing under 35 U.S.C. 371 from International Application No. PCT/US2017/058801, filed on Oct. 27, 2017, and published as WO 2018/081591 on May 3, 2018, which application claims the benefit of priority from U.S. Provisional Patent Application Ser. No. 62/414,332, filed on Oct. 28, 2016 and U.S. Provisional Patent Application Ser. No. 62/453,402, filed on Feb. 1, 2017, which are herein incorporated by reference.

FIELD

Embodiments disclosed herein include topical compositions, such as a cosmetic, that includes a combination of retinol and a plant extract such as an extract from alfalfa, and uses thereof.

BACKGROUND

The art is continually seeking new topical compositions that are storage stable, easily applied, and effective to combat a variety of disorders.

SUMMARY

The present invention relates to topical compositions comprising at least one retinoid, and at least one plant extract, such as an extract from alfalfa, and at least one carrier and uses thereof.

BRIEF DESCRIPTION OF FIGURES

FIG. 1 provides a table depicting CRABPII gene expression in treated compared to untreated human fibroblast cells. Normal human fibroblasts were treated with ingredients described herein for 24 hours. Gene expression of CRABPII, a retinoic-acid receptor, was quantified by using Real-Time RT-PCR. The gene expression was compared with untreated cells.

DETAILED DESCRIPTION

Embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In addition, it is to be understood that the phraseology or terminology employed herein, and not otherwise defined, is for the purpose of description only and not of limitation.

All percentages and ratios used herein are by weight of the total composition and all measurements made are at 25° C., unless otherwise designated.

All numeric ranges are inclusive of narrower ranges; delineated upper and lower range limits are interchangeable to create further ranges not explicitly delineated. The number of significant digits conveys neither limitation on the indicated amounts nor on the accuracy of the measurements.

In this document, the terms "a" or "an" are used to include one or more than one and the term "or" is used to refer to a nonexclusive "or" unless otherwise indicated. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

The term "topical application," as used herein, means to apply or spread the compositions of the present invention onto the surface of the skin and also hair, nails and other mammalian, such as human, keratinous tissue.

The phrase "dermatologically-acceptable," as used herein, means that the compositions or components thereof so described are suitable for use in contact with human skin without undue toxicity incompatibility, instability, allergic response, and the like.

The phrase "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound judgment of the skilled artisan.

"Skin care actives" as used herein, means substances that when applied to the skin, provide a benefit or improvement to the skin. It is to be understood that skin care actives are useful not only for application to skin, but also to hair, nails and other mammalian keratinous tissue.

"Situs" means the location where the composition is applied. Non-limiting examples of a situs include mammalian, such as human, keratinous tissue.

As used herein, the term "purified" and like terms relate to an enrichment of a molecule or compound relative to other components associated with the molecule or compound. The term "purified" does not necessarily indicate that complete purity of the particular molecule has been achieved during the process.

The term "substantially pure" describes a compound which has been separated from components which accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, is also substantially purified when it is essentially free of associated components or when it is separated from the native contaminants which accompany it in its natural state.

The terms "comprises," "comprising," and the like can have the meaning ascribed to them in U.S. Patent Law and can mean "includes," "including" and the like. As used herein, "including" or "includes" or the like means including, without limitation.

Composition

Retinoid

The compositions of the present invention can include a retinoid or retinoid like compound. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and Reissue 34,075, issued Sep. 22, 1992 to Purcell et al. Other suitable retinoids are tocopheryl-retinoate (tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). One or more retinoids may be used herein. Preferred retinoids are retinol, retinyl palmitate, retinyl acetate, retinyl proprionate, retinal and combinations thereof. More preferred are retinol and retinyl palmitate.

The retinoid may be included as a substantially pure material, or as an extract obtained by suitable physical and/or chemical isolation from natural (e.g., plant) sources.

The compositions of this invention can contain a safe and effective amount of the retinoid for regulating a skin condition, preferably for regulating visible and/or tactile discontinuities in skin, more preferably for regulating signs of skin aging, even more preferably for regulating visible and/or tactile discontinuities in skin texture associated with skin aging. The compositions preferably contain from about 0.000001-0.3%, including about 0.005% to about 2%, more preferably 0.01% to about 2%, retinoid. Retinol is most preferably used in an amount of from about 0.01% to about 0.3%; retinol esters are most preferably used in an amount of from about 0.01% to about 2% (e.g., about 1%); retinoic acids are most preferably used in an amount of from about 0.01% to about 0.3%; tocopheryl-retinoate [tocopherol ester of retinoic acid (trans- or cis), adapalene {6-[3-(1-adamantyl)4-methoxyphenyl-2-naphthoic acid}, and tazarotene are most preferably used in an amount of from about 0.01% to about 2%.

Plant Extracts

The compositions of the present invention can include extracts from plants, including, but not limited to, alfalfa plants, olive plants and coconut plants.

Methods of preparing an extract from plants, such as alfalfa, are well known and any method available to an art worker is suitable.

For example, in one embodiment, the raw materials may be collected from the whole of the plants, such as alfalfa plants (*Medicago sativa*) (i.e. stems, leaves, roots, flowers, etc.), and in certain embodiments the raw materials are primarily or solely obtained from the leaves and stems of plants, such as alfalfa. In certain embodiments, the raw materials collected from the plants are ground to small particle sizes. In addition, the raw materials may be dried to reduce water content. The raw materials may be air-dried, oven-dried, rotary evaporated under vacuum, lyophilized, or dried by any other suitable method available to an art worker.

The extract of plants, such as alfalfa, may be obtained by distilling the raw materials with a stripping agent. The stripping agent may be a liquid that is miscible, immiscible, or partially miscible with the desired extract from, for example, alfalfa. Suitable stripping agents include, but are not limited to the following: water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. In one embodiment, the stripping agent is immiscible with the desired extract from plants, including alfalfa. The plant extract may be collected by phase separation from the stripping agent.

In other embodiments, plant botanical component may be in the form of an extract obtained by solvent extraction, in one embodiment obtained by an organic solvent extraction. Briefly, the organic solvent extraction method involves washing and extracting the raw materials, which may be whole or ground into small particle sizes, using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field. The raw materials are pushed slowly into the extracting machine by a thruster. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the plant (e.g., alfalfa) constituents is used, typically between about 1-10 hours, in one embodiment between about 2-8 hours, and in one embodiment between about 3-6 hours. The temperature of extraction is between about 30° C.-100° C., in one embodiment between about 40° C.-70° C., and in one embodiment between about 50° C.-60° C. The collected extract is then fine-filtered to remove debris, and may be used directly, or is concentrated, for example by distilling the solvent or by other conventional processing. The solution of extract actives may be rotary evaporated under vacuum or lyophilized. A typical extract's actives content is above about 25%, in one embodiment above 50%, and the extract may also be provided as an essential oil or a concentrate having a semi-solid or solid consistency.

Similarly, aqueous-organic solvent extraction involves initially collecting raw materials from the plants, such as alfallfa, which may be whole or ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH. depending on the acidity or alkalinity of the collected extract. The aqueous extract may be used directly, in concentrated or dried form. Alternatively, organic solvent may then be added to the neutralized solution to transfer the extract from an aqueous phase to an organic phase. Examples of such organic solvents include, but are not limited to, ethanol, isopropanol, butanol, pentanol, hexanol, and xylene. The extract comprising the transferred extract actives dissolved in organic solvent may be used directly as an essential oil or a concentrate, or dried by a number of different means, such as, for example, air-drying, oven-drying, rotary evaporating under vacuum or lyophilizing to a semi-solid or solid consistency.

It should also be noted that different plants containing different constituents can be mixed and extracted together with the alfalfa. This process of mixed extraction can in one embodiment be used for extracting those plants containing constituents with similar solubility as alfalfa in the solvent used for extraction, such as ethanol. The mixture of extracts can be concentrated and stored in an appropriate solvent.

In one embodiment, it is a complex of fractions from an extract from Alfalfa, lipids from olives and hydrocarbons from coconut oil.

In one embodiment, the composition comprises lipids, such as lipids from olives (e.g., otnega-9, monounsaturated fatty acids: oleic acid, palmitoleioc acid; omega-6, polyunsaturated fatty acids: linoleic acid, saturated fats: palmitic, steric acid; trace lipids linolenic, arachidic, eicosenoic, heptadecanoic, behenic, lignoceric and myristic acids) (or lipids from other plants), including squalene.

In another embodiment, the composition comprises coconut oil (e.g., all components of coconut oil) and/or hydrocarbons, such as hydrocarbons from coconut oil.

The compositions of this invention can contain a safe and effective amount of a plant extract (e.g., obtained from alfalfa), squalene and coconut oil for regulating a skin condition, preferably for regulating visible and/or tactile discontinuities in skin, more preferably for regulating signs of skin aging, even more preferably for regulating visible and/or tactile discontinuities in skin texture associated with skin aging. The compositions preferably contain from about 0.0005-3.0%, including about 0.005% to about 2%, including 0.01% to about 2%, of a combination of alfalfa extract, squalene and coconut oil or each one individually (for example, from 0.005% to 1%, including 0.005% and 1%)

The combination of alfalfa extract, squalene and coconut oil can be found in "Chloroplastim," which refers to a formulation that includes an extract from alfalfa, squalene from olives and coconut oil. One manufacturer can be Barnet.

Carrier

The compositions of the present invention comprise from about 1% to about 99.7% of an acceptable carrier within which the retinoid (e.g., retinol of about 0.25%) and alfalfa extract/squalene/cocortut oil component (e.g., about 0.1%) and additional materials are incorporated to enable these components to be applied/delivered topically at an appropriate concentration. The carrier can thus act as a diluent, dispersant, solvent, or the like for the particulate material which ensures that it can be applied to and distributed evenly over the selected target at an appropriate concentration.

The carrier may contain one or more dermatologically acceptable solid, semi-solid or liquid fillers, diluents, solvents, extenders and the like. The carrier may be solid, semi-solid or liquid.

The carrier can be substantially liquid. The carrier can itself be inert or it can possess dermatological benefits of its own. Concentrations of the carrier can vary with the carrier selected and the intended concentrations of the components.

Suitable carriers include conventional or otherwise known carriers that are dermatologically acceptable. The carrier should also be physically and chemically compatible with the essential components described herein, and should not unduly impair stability, efficacy or other use benefits associated with the compositions of the present invention. Preferred components of the compositions of this invention should be capable of being comingled in a manner such that there is no interaction which would substantially reduce the efficacy of the composition under ordinary use situations.

The type of carrier utilized herein depends on the type of product form desired for the composition. The topical compositions useful in the subject invention may be made into a wide variety of product forms such as are known in the art. These include, but are not limited to, lotions, creams, gels, sticks, sprays, ointments, oils, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and oils.

Carriers can contain a dermatologically acceptable diluent. As used herein, "diluent" includes materials in which the material can be dispersed, dissolved, or otherwise incorporated, such as a lipophilic diluent/carrier. Solutions according to the subject invention typically include a dermatologically acceptable diluent. Solutions useful in the subject invention can contain from about 60% to about 99.99% of the diluent.

Aerosols according to the subject invention can be formed by adding a propellant to a solution such as described above. Exemplary propellants include chloro-fluorinated lower molecular weight hydrocarbons, Additional propellants that are useful herein are described in Sagarin, Cosmetics Science and Technology, 2nd Edition, Vol. 2, pp. 443-465 (1972), incorporated herein by reference. Aerosols are typically applied to as a spray-on product.

Carriers can comprise an emulsion comprising a hydrophilic phase comprising a hydrophilic component, e.g., water or other hydrophilic diluent, and a hydrophobic phase comprising a hydrophobic component, e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 50% of the dispersed hydrophobic phase and from about 1% to about 98% of the continuous hydrophilic phase; water-in-oil emulsions typically comprise from about 1% to about 98% of the dispersed hydrophilic phase and from about 1% to about 50% of the continuous hydrophobic phase. The emulsion may also comprise a gel network, such as described in "Application of Emulsion Stability Theories to Mobile and Semisolid Oil-in-Water Emulsions", Cosmetics and Toiletries, vol. 101, November, 1986, pp. 73-92, which is incorporated by reference herein. Preferred emulsions are further described below.

The topical compositions of the subject invention, including but not limited to lotions, oils and creams, may comprise a dermatologically acceptable emollient. Such compositions can contain from about 2% to about 50% of the emollient. Emollients tend to lubricate the skin, increase the smoothness and suppleness of the skin, prevent or relieve dryness of the skin, and/or protect the skin. Emollients are typically water-immiscible, oily or waxy materials. A wide variety of suitable emollients are known and may be used herein. Sagarin, Cosmetics, Science and Technology 2nd Edition, Vol. 1, pp. 32-43 (1972), incorporated herein by reference, contains numerous examples of materials suitable as an emollient.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water. A cream typically comprises from about 5% to about 50%, preferably from about 10% to about 20%, of emollient; and from about 45% to about 85%, preferably from about 50% to about 75%, water.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, Cosmetics, Science and Technology. 2nd Edition, Vol. 1, pp. 72-73 (1972), incorporated herein by reference, and/or an emollient. For example, an ointment may comprise from about 2% to about 10% of an emollient; and from about 0.1% to about 2% of a thickening agent.

Compositions of this invention useful for cleansing ("cleansers") are formulated with a suitable carrier, e.g., as described above, and preferably contain one or more dermatologically acceptable surfactants in an amount which is safe and effective for cleansing. For example, such compositions contain from about 1% to about 90%, more preferably from about 5% to about 10%, of a dermatologically acceptable surfactant. The surfactant is can be selected from anionic, cationic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, sodium lauryl sulfate, and betaines such as described herein. See U.S. Pat. No. 4,800,197, to Kowez et al., issued Jan. 24, 1989, which is incorporated herein by reference in its entirety, for exemplary surfactants useful herein. Examples of a broad variety of additional surfactants useffil herein are described in McCutcheon's Detergents and Emulsifiers, North American Edition (1986), published by Allured Publishing Corporation, which is incorporated herein by reference in its entirety. The cleansing compositions can optionally contain, at their art-established levels, other materials which are conventionally used in cleansing compositions.

The physical form of the cleansing compositions can be, for example, formulated as bars, liquids, shampoos, bath gels, hair conditioners, hair tonics, pastes, or mousses. Bars are most preferred since this is the form of cleansing agent most commonly used to wash the skin. Preferred rinse-off cleansing compositions, such as shampoos, include a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989, incorporated herein by reference in its entirety.

The composition may also take the form of a cosmetic composition that may be applied to mammalian keratinous tissue, including human skin. The cosmetic compositions may take various forms. For example, some non-limiting examples of forms include solutions, suspensions, lotions, oils, creams, gels, toners, sticks, pencils, ointments, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

For example, the cosmetic composition may comprise from 1% to 95% by weight of water. The cosmetic composition may comprise from 1% to 95% by weight of one or more oils. Oils may be used to solubilize, disperse, or carry materials that are not suitable for water or water soluble solvents. Suitable oils include silicones (such as dimethicone), hydrocarbons, esters, amides, ethers, and mixtures thereof. When the cosmetic composition is in the form of an emulsion, oils are carriers typically associated with the oil phase. The cosmetic composition may be in the form of a water-in-oil emulsion, an oil-in-water emulsion, or a water-in-silicone emulsion such that the cosmetic composition may include water, a silicone, oil, and combinations thereof. The cosmetic compositions may include an emulsifier. An emulsifier is particularly suitable when the cosmetic composition is in the form of an emulsion or if immiscible materials are being combined. The cosmetic composition may comprise from 0.05%, 0.1%, 0.2%, 0.3%, 0.5%, or 1% to 20%, 10%, 5%, 3%, 2%, or 1% emulsifier, Emulsifiers may be nonionic, anionic, zwitterionic, or cationic. Structuring agents may be used to increase viscosity, thicken, solidify, or provide solid or crystalline structure to the cosmetic composition. Structuring agents are typically grouped based on solubility, dispersibility, and phase compatibility. Examples of aqueous or water structuring agents include, but are not limited to, polymeric agents, natural or synthetic gums, polysaccharides, and the like. The cosmetic compositions may comprise from 0.0001%, 0.001%, 0.01%, 0.05%, 0.1%, 0.5%, 1%, 2%, 3%, 5% to 25%, 20%, 10%, 7%, 5%, 4%, or 2%, by weight of the cosmetic composition, of one or more structuring agents. The cosmetic compositions may optionally contain one or more UV actives. As used herein, "UV active" includes both sunscreen agents and physical sunblocks. Suitable UV actives may be organic or inorganic. Examples of some suitable UV actives are listed in the functional category of "Sunscreen Agents" in the Personal Care Product Council's *International Cosmetic Ingredient Dictionary and Handbook*, Thirteenth Edition, 2010. The cosmetic compositions may be generally prepared by conventional methods such as those known in the art of making cosmetic compositions. Such methods typically involve mixing of ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The cosmetic compositions are preferably prepared such as to optimize stability (physical stability, chemical stability, photostability, etc.) and/or delivery of active materials. The cosmetic composition may be provided in a package sized to store a sufficient amount of the cosmetic composition for a treatment period. The size, shape, and design of the package may vary widely.

The cosmetic compositions disclosed herein may be applied to one or more skin surfaces and/or one or more mammalian, such as human, keratinous tissue surfaces as part of a user's daily routine or regimen. Additionally or alternatively, the cosmetic compositions herein may be used on an "as needed" basis. In some examples, an effective amount of the cosmetic composition may be applied to the target portion of the keratinous tissue or skin. In some examples, the cosmetic composition may be provided in a package with written instructions detailing the application regimen.

Uses Thereof

The compositions of the present invention are useful for topical application, such as a cosmetic and for regulating a skin condition, including visible and/or tactile discontinuities in skin. Such discontinuities may be induced or caused by internal and/or external factors, and include the signs of skin aging described herein. The term "regulating skin condition" includes prophylactically regulating and/or therapeutically regulating skin condition, including visible and/or tactile discontinuities in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel.

The compositions of the present invention are useful for regulating signs of skin aging, more especially visible and/or tactile discontinuities in skin texture associated with aging. "Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnoual differentiation, hyperkeratinization, elastosis, collagen breakdown, and other histological changes in the stratum corneum, detmis, epidermis, the skin vascular system (e.g., telangiectasia or spider vessels), and underlying tissues, especially those proximate to the skin.

It is to be understood that the present invention is not to be limited to regulation of the above mentioned "signs of skin aging" which arise due to mechanisms associated with skin aging, but is intended to include regulation of said signs irrespective of the mechanism of origin. As used herein, "regulating skin condition" is intended to include regulation of such signs irrespective of the mechanism of origin.

The present invention is especially useful for therapeutically regulating visible and/or tactile discontinuities in mammalian, such as human, skin texture, including texture discontinuities associated with skin aging. As used herein, therapeutically regulating such discontinuities includes ameliorating, e.g., diminishing, minimizing and/or effacing visible and/or tactile discontinuities in the texture of mammalian, human skin, to thereby provide improved skin appearance and/or feel, e.g., a smoother, more even appearance and/or feel. Such visible and/or tactile discontinuities in skin texture include crevices, bumps, pores, fine lines, wrinkles, scales, flakes and/or other for us of textural unevenness or roughness associated with skin aging. For example, the length, depth, and/or other dimension of lines and/or wrinkles are decreased, the apparent diameter of pores decreases, or the apparent height of tissue immediately proximate to pore openings approaches that of the interadnexal skin.

The present invention is also especially useful for prophylactically regulating visible and/or tactile discontinuities in mammalian, such as human, skin texture, including texture discontinuities associated with skin aging. As used herein, prophylactically regulating such discontinuities includes delaying, minimizing and/or preventing visible and/or tactile discontinuities in the texture of mammalian skin, to thereby provide improved skin appearance and/or feel, e.g., a smoother, more even appearance and/or feel.

The compositions described herein can used to treat and/or prevent a variety of skin conditions and/or disorders. Skin conditions/disorders can include aging, signs of aging, acne, dermatitis, rosacea, psoriasis. Signs of aging can include wrinkles, fine lines, wizened skin, skin laxity associated with collagen loss or destruction, loss or reduction in skin integrity, lack of skin elasticity, lack of skin tone, thinned skin, sagging skin, skin suffering from degradation of collagen fibers, flaccid skin, and/or skin suffering from internal degradation. The conditions/disorders can include inflammation, broken veins, redness, blotchiness, puffy eyes or dark circles, or skin pigmentation disorders. The composition provided herein are also useful for skin lightening, for improving wound healing, for promoting youthful looking skin, for promoting evenness of skin tone by reducing skin redness or inflammation or UV induced skin redness, blotchiness or inflammation, for lightening the color of the skin or scalp, for promoting skin regeneration to produce more homogenous, firmer, more toned and more elastic skin, for promoting cell longevity, for promoting skin brightness, for promoting skin texture and tone uniformity and/or for reducing the appearance of skin pigmentation and/or skin darkening, for treating or preventing ulcerated areas or areas of cutaneous stress or damage brought about by exposure to UV or exposure to an irritant product, for enhancing skin desquamation, improving skin hydration, improving skin luster and brightness, or for treating or reducing acne or other skin blemishes.

The compositions disclosed herein may be applied to one or more topical surfaces and/or one or more mammalian, such as human, keratinous tissue surfaces as part of a user's daily routine or regimen. Additionally or alternatively, the compositions herein may be used on an "as needed" basis and used for as intended for the given consumer product. The composition may be applied to any article, such as a textile, or any absorbent article.

The following examples are intended to further illustrate certain embodiments of the invention and are not intended to limit the scope of the invention in any way.

Exemplary compositions of this invention include:

One formulation disclosed herein includes retinol and alfalfa extract/squalene/coconut oil:

| Phase | Ingredient | % w/w |
| --- | --- | --- |
| Phase A | cyclopentasiloxane | QS |
|  | dimethicone | 1.00-10.00 |
| Phase B. | Bisabolol | 0.25-3.00 |
|  | Tetrahexyldecyl ascorbate | 0.025-5.00 |
|  | Tocopherylacetate | 0.25-3.00 |
| Phase C | C(12-15) alkyl benzoate | 0.1-2.00 |
|  | Retinol | 0.000001 to 0.300 |
|  | alfalfa extract/squalene/coconut oil | 0.0005 to 3.00 |
|  | Argan Oil | 0.25-3.00 |
|  | Olive Oil | 0.000001 to 0.300 |
|  | *Carthamus tinctorius* (safflower) seed oil | 0.000001 to 0.300 |
|  | *Plukenetia volubilis* seed oil | 0.000001 to 0.300 |

In one embodiment, the formulations disclosed herein can be used alone or impregnated into fibrous, cellulosic pads for application to skin. One embodiment consists essentially of retinol and alfalfa extract/squalene/coconut oil (in one embodiment, such a composition is impregnated into fibrous, cellulosic pads for application). In one embodiment, the alfalfa extract/squalene/coconut oil complex comprises about 50-70% squalene, about 15-25% alfalfa extract (e.g. *Medicago sativa* extract), and about 15-25% coconut oil (*Cocos mucifera* oil).

For other embodiments, Phase A includes cyclotetrasiloxane and/or cyclohexasiloxane in lieu of the cyclopentasiloxane.

The alfalfa extract/squalene/coconut oil complex of Phase C includes squalene, *Medicago* alfalfa extract, and *Cocos nucifera* (coconut) oil, and can be obtained from Barnet. For some embodiments, the retinol to alfalfa extract/squalene/coconut oil ratio is 0.25%/0.1 to 1%.

EXAMPLE 1

FIG. 1 provides a table depicting CRABPII gene expression in treated compared to untreated human fibroblast cells (very small doses were used directly on cells to avoid any toxicity). Normal human fibroblasts were cultivated with culture medium (Dulbecco Modified Eagle Medium+Fetal calf serum) and were treated with ingredients described herein for 24 hours. Non treated cells were incubated under the same conditions. Gene expression of CRABPII, a retinoic-acid receptor, was quantified by using Real-Time RT-PCR.

Total mRNA were extracted by using Kingfisher Pure RNA Tissue kit with the KingFisher Flex (Thermo) and quantified with a spectrophotometer at 260 nm. First strand cDNA synthesis was performed with the High cDNA reverse transcription kit (Thermo). Real-Time PCR was carried out with the 7300 Real Time PCR System by using the TaqMan primers and probes specific to CRABPII. Relative changes in gene expression were calculated according to the $2^{-\Delta\Delta CT}$ method. The gene expression was compared with untreated cells.

EXAMPLE 2

The effect of alfalfa extract/squalene/coconut oil and retinol on stimulation of the collagen I synthesis on Normal Human Fibroblasts can be studied by Western blot. Normal Human fibroblasts (NHDF) will be treated for 6 days with the mix of active ingredients, alfalfa extract/squalene/coconut oil and retinol, diluted in culture medium with a reapplication of the active ingredients after 72 H. The collagens can be extracted (with pepsin). Collagen I can be detected by using an immunoblotting method with a chemiluminescence detection kit. The intensity of the bands of collagen I obtained on the treated cells can be compared to the intensity of the bands of the non-treated cells by a visual method by two experts according to established criteria. The alfalfa extract/squalene/coconut oil and retinol doses can be determined with a cytotoxicity test (by the neutral red method).

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description. All publications, patents, and patent documents referred to in this document are incorporated by reference herein in their entirety, as though individually incorporated, by reference. In the event of inconsistent usages between this document and those documents so incorporated by reference, the usage in the incorporated reference should be considered supplementary to that of this document; for irreconcilable inconsistencies, the usage in this document controls.

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

The invention claimed is:

1. A formulation comprising:

| Phase | Ingredient | % w/w |
|---|---|---|
| Phase A | cyclopentasiloxane | QS |
| | dimethicone | 1.00-10.00 |
| Phase B. | Bisabolol | 0.25-3.00 |
| | Tetrahexyldecyl ascorbate | 0.025-5.00 |
| | Tocopherylacetate | 0.25-3.00 |
| Phase C | C(12-15) alkyl benzoate | 0.1-2.00 |
| | Retinol | 0.000001 to 0.300 |
| | alfalfa extract/squalene/coconut oil | 0.0005 to 3.00 |
| | Argan Oil | 0.25-3.00 |
| | Olive Oil | 0.000001 to 0.300 |
| | *Carthamus tinctorius* (safflower) seed oil | 0.000001 to 0.300 |
| | *Plukenetia volubilis* seed oil | 0.000001 to 0.300. |

2. The formulation of claim 1, wherein the formulation is formulated as a cosmetic, cream, lotion, oil or gel.

3. A method for reducing the appearance of wrinkles on skin comprising topically applying to said wrinkles the formulation of claim 1.

4. The method of claim 3, wherein the wrinkles are present on facial skin, arm skin, hand skin, or neck skin.

5. A method for treating at least one sign of skin ageing or at least one sign of a skin damage condition associated with ageing, comprising topically administering the formulation of claim 1.

6. The method according to claim 5, wherein the at least one sign of skin ageing or the at least one sign of skin damage condition is produced by intrinsic biological aging or photo-induced ageing.

7. A pad impregnated with the formulation of claim 1.

8. The pad of claim 7, wherein the pad is a fibrous, cellulosic pad.

* * * * *